United States Patent [19]
Wolozin et al.

[11] Patent Number: 5,869,266
[45] Date of Patent: Feb. 9, 1999

[54] HUMAN OLFACTORY NEURON CULTURES TO DIAGNOSE ALZHEIMER'S DISEASE

[75] Inventors: Benjamin L. Wolozin, Columbia; Hayden G. Coon, Gaithersburg, both of Md.

[73] Assignee: The United States of America as represented by the Department of Health and Human Services, Washington, D.C.

[21] Appl. No.: 605,788

[22] Filed: Oct. 30, 1990

Related U.S. Application Data

[63] Continuation-in-part of Ser. No. 487,894, Mar. 6, 1990, abandoned.

[51] Int. Cl.$^6$ .................................................. G01N 33/53
[52] U.S. Cl. .................... 435/7.21; 435/325; 435/368; 436/503; 436/63; 436/811
[58] Field of Search ................ 436/503, 63, 86, 436/811; 435/1, 30, 7.1, 7.21, 29, 243, 240.1, 240.21, 325, 368

[56] References Cited

U.S. PATENT DOCUMENTS 4,829,000  5/1989  Kleinman et al. .

OTHER PUBLICATIONS

Montgomery et al., Developmental Biology 117, 64–70 (1986) Morphogenesis in Vitro of Dissociated Fetal Rat Small Intestinal Cells upon an Open Surface and Subsequent to Collagen Gel Overlay.
Calof et al. *Neuron* 3: 115–127, 1989.
Wolozin et al. *Science* 232: 648–650, 1986.
Cole et al. *Biochem. Biophys. Res. Comm.* 170(1): 288–295, 1990.
Kleinman et al in *The Role of Extracellular Matrix in Development*, Alan R. Liss, Inc.: New York, pp. 123–143 (1984).
Lovell et al. Arch. Otolaryngol. 108: 247–249, 1982.
Yankner et al. *Science* 245: 417–420, 1989.
The Washington Post, "Tracking Alzheimer's: Tangles in Brain Cells Believed to Hold Key", 25 Feb. 1991.
Mari, J., Science, vol. 249, pp. 984–985 (31 Aug. 1990).
Talamo et al., Nature, vol. 337(23), pp. 736–739 (Feb. 1989).
Mita et al., Biological Abstracts, Abstract #85113, vol. 88 (1989).
Serby et al. "Olfactory Dysfunction in Alzheimer's Disease and Parkinsons' Disease" Am. J. Psychiatry vol. 142:6. Jun. 1985 pp. 781–782.
Coon et al. "Cell Cultures of Neuroblasts from Rat Olfactory Epithelium that Show Odorant Responses" Proc. Natl. Academy Sci. USA vol. 86 Mar. 1989 pp. 1703–1707.
Tomonaga et al. "Approach to Dementia Research". Rinsho Shinkeigaku, vol. 29 (12) Dec. 1989 pp. 1532–1535 (Abstract).
Card et al. "Immunocytochemical Localization of the Precursor Protein for Beta–Amyloid in the Rat Central Nervous System" Neuron vol. 1(9) Nov. 1988 pp. 835–846 (Abstract).
Mann et al "Alzheimer's Disease and Olfactory Connection?" Mech Ageing Dev. vol. 42 (1) 1988 pp. 1–16 (Abstract).
Takahashi et al "Progressive Supranuclear Palsy with Limbic System Involvement Report of a Case With Ultrastructural Investigation of Neurofibrillary Tangles in Various Locations" Clinical Neuropathology vol. 6(6) 1987 pp. 271–276 (Abstract).
Ohm et al. "Olfactory Bulb Changes in Alzheimer's Disease" Acta Neuropathologica. vol. 73 (4) 1987 pp. 365–369 (Abstract).

*Primary Examiner*—Patricia Duffy
*Attorney, Agent, or Firm*—Morgan & Finnegan, LLP

[57] ABSTRACT

The present invention relates to a culture of human olfactory neurons. The neurons may display a normal neuronal pathology or a pathology characteristic of a generalized central nervous system disease. The cultured neurons can be used for neurotoxicity tests, screening for therapeutic drugs and anti-viral agents, and diagnosing Alzheimer's disease.

3 Claims, 6 Drawing Sheets

HUMAN OLFACTORY NEURON CULTURES TO DIAGNOSE ALZHEIMER'S DISEASE

BACKGROUND OF THE INVENTION

This is a continuation-in-part application of Ser. No. 07/487,894 filed on Mar. 6, 1990, now abandoned which is herein incorporated in its entirety by reference.

1. FIELD OF THE INVENTION

The present invention relates to cultures of human olfactory neurons and to methods of screening agents for therapeutic and toxic effects using such cultures.

2. BACKGROUND INFORMATION

Neurons have eluded the attempts of researchers to maintain them in continuous cultures largely because most neurons do not divide and/or proliferate. Investigators have been able to maintain fetal or newborn rat neurons in culture, however, the neurons are static, do not divide and die after several months.

Olfactory sensory neurons, which are of central origin and are considered part of the central nervous system, do divide [Talamo et al., Nature 337:736–739, (1989)]. In fact, olfactory neurons from rats have been cultured [Coon et al., PNAS USA 86:1703–1707, (1989)]. However, rats do not develop human neurologic diseases, such as Alzheimer's disease and other human mental illnesses. Therefore, cultures of rat neurons can not be used to test for potential therapeutic agents for these human diseases. Furthermore, rats have different tolerance levels of toxic compounds than humans. Therefore, the neurotoxicity of various agents to humans could be more accurately determined using cultured human neurons than cultured rat neurons.

Cell cultures of cancer cells, such as human neuroblastoma cells, also exist. However, these cells tend to be undifferentiated and do not exhibit a strong neuronal phenotype. Neuroblastomas are not of central nervous system origin. Furthermore, neuroblastomas have not been cultured from individuals with generalized central nervous system diseases (ie, neuro/psychiatric illnesses).

Human olfactory neurons, being primarily, of central nervous system origin from healthy individuals and individual with neuro/psychiatric illnesses would offer better systems for testing agents for therapeutic and toxic effects.

SUMMARY OF THE INVENTION

Accordingly, it is an object of the present invention to provide human olfactory neuron cultures from individuals without central nervous system diseases and from individuals with diseases of the central nervous system.

It is another object of the present invention to provide a method for assessing the potential neurotoxicity and potential therapeutic effects of agents in humans without employing live animals.

It is a further object of the present invention to provide a method for studying generalized diseases of the central nervous system.

Various other object and advantages of the present invention will be apparent from the drawings and the following description of the invention.

In one embodiment, the present invention relates to a culture of replicating mammalian olfactory neurons, such as human. The neurons may display normal neuronal pathology or they may display pathology characteristic of a central nervous system disease.

In another embodiment, the present invention relates to a method of replicating mammalian olfactory neurons comprising contacting mammalian neurons with a growth medium and maintaining the neurons and medium under conditions allowing replication.

In a further embodiment, the present invention relates to a method of screening drugs for their ability to reverse or eliminate expression of central nervous system disease pathology comprising contacting cultured human neurons which show pathological characteristics of a central nervous system disease with a drug under conditions such that reversal or elimination of the disease pathology can be effected.

In yet another embodiment, the present invention relates to a method of screening drugs for their ability to inhibit virus activity on neurons comprising contacting cultured human neurons with a drug under conditions such that inhibition of viral function can be effected.

In yet a further embodiment, the present invention relates to a method of testing for neurotoxicity of an agent comprising contacting replicating human olfactory neurons with an agent and determining the toxic effect of the agent on the neurons.

In another embodiment, the present invention relates to a method of diagnosing Alzheimer's disease. Human tissue containing olfactory neurons is isolated and the tissue is grown in a suitable medium under a first membrane comprising collagen or laminin. The neurons are then separated from the first membrane and replaced on a surface coated with a second membrane comprising collagen or laminin. The neurons are then cultured under conditions allowing replication. The culturing neurons are contacted with a calcium salt and then with a calcium ionophore. The presence or absence of Alzheimer's specific protein are then detected.

BRIEF DESCRIPTION OF THE DRAWINGS

The file of this patent contains at least one drawing executed in color.

FIG. 1 shows the morphology of neurons grown in culture under conditions allowing for growth in three dimensions.

DETAILED DESCRIPTION OF THE PREFERRED EMBODIMENT

Figure 1A:
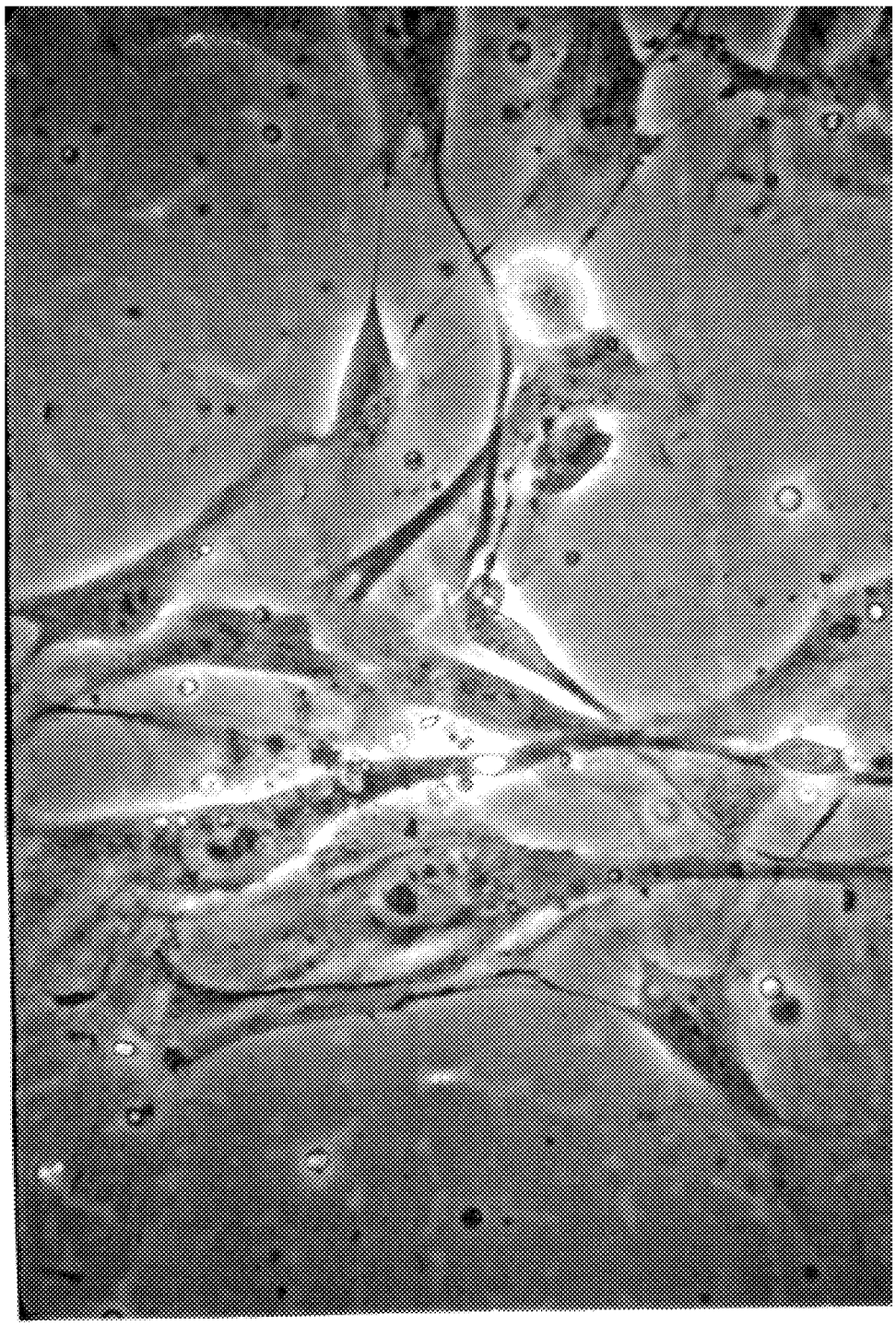
FIG. 1A shows the same neurons when grown on a basement membrane coated flat surface.
Figure 1B:
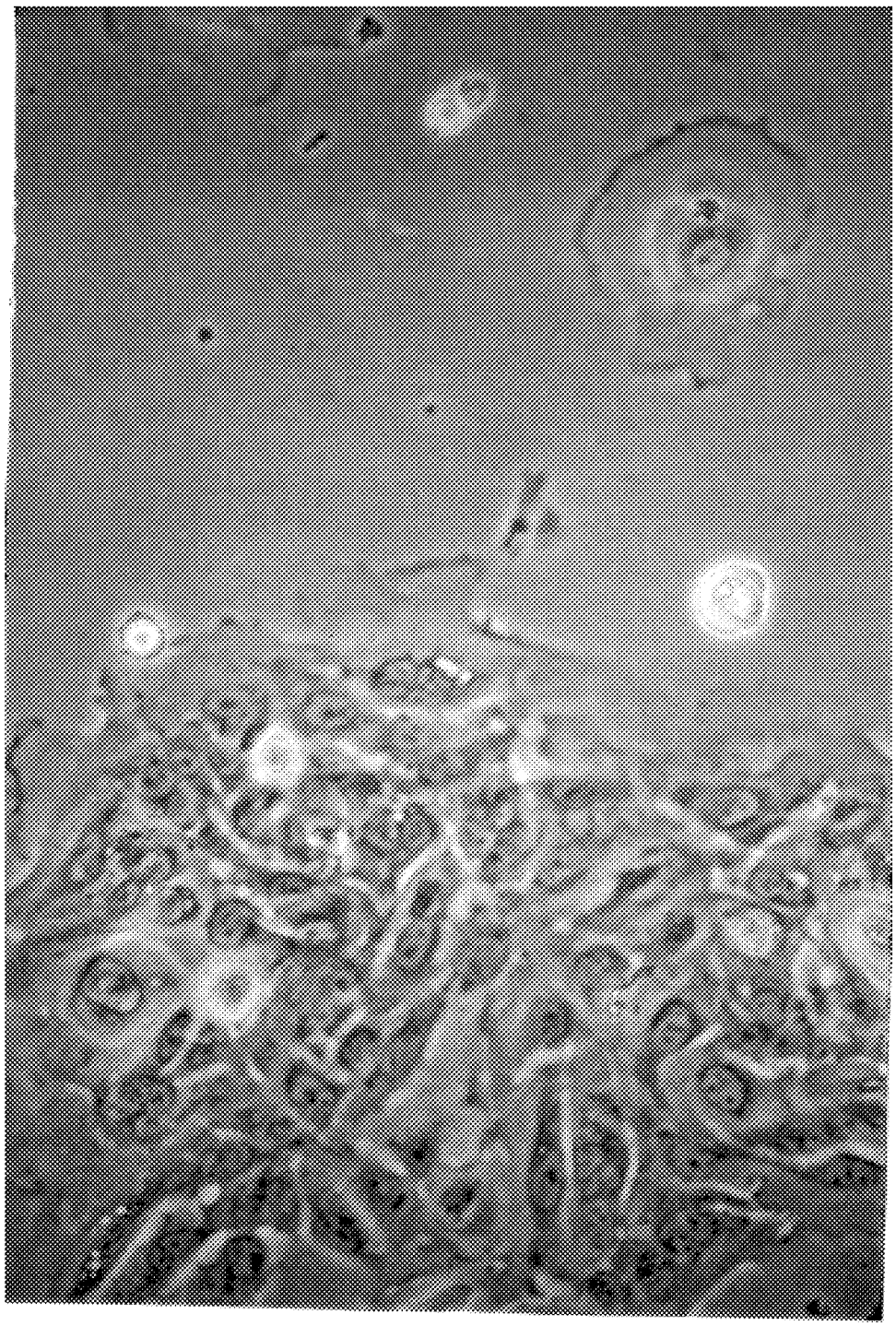
FIG. 1B shows epithelial cells grown from the tissue sample on a basement membrane coated flat surface.
Figure 1C:
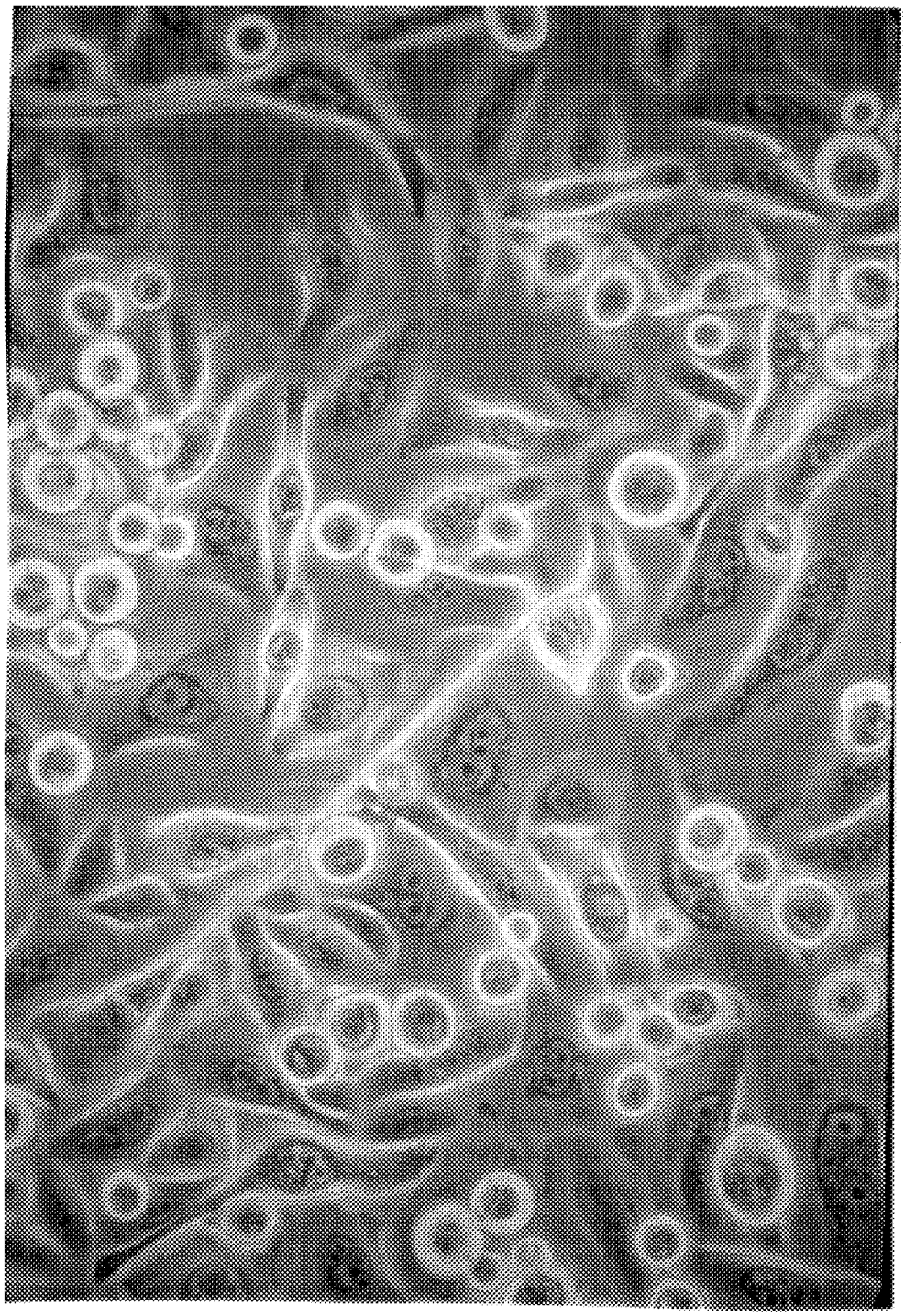
FIGS. 1C–E show other cells not fully characterized grown on a basement membrane coated flat surface.
Figure 1D:
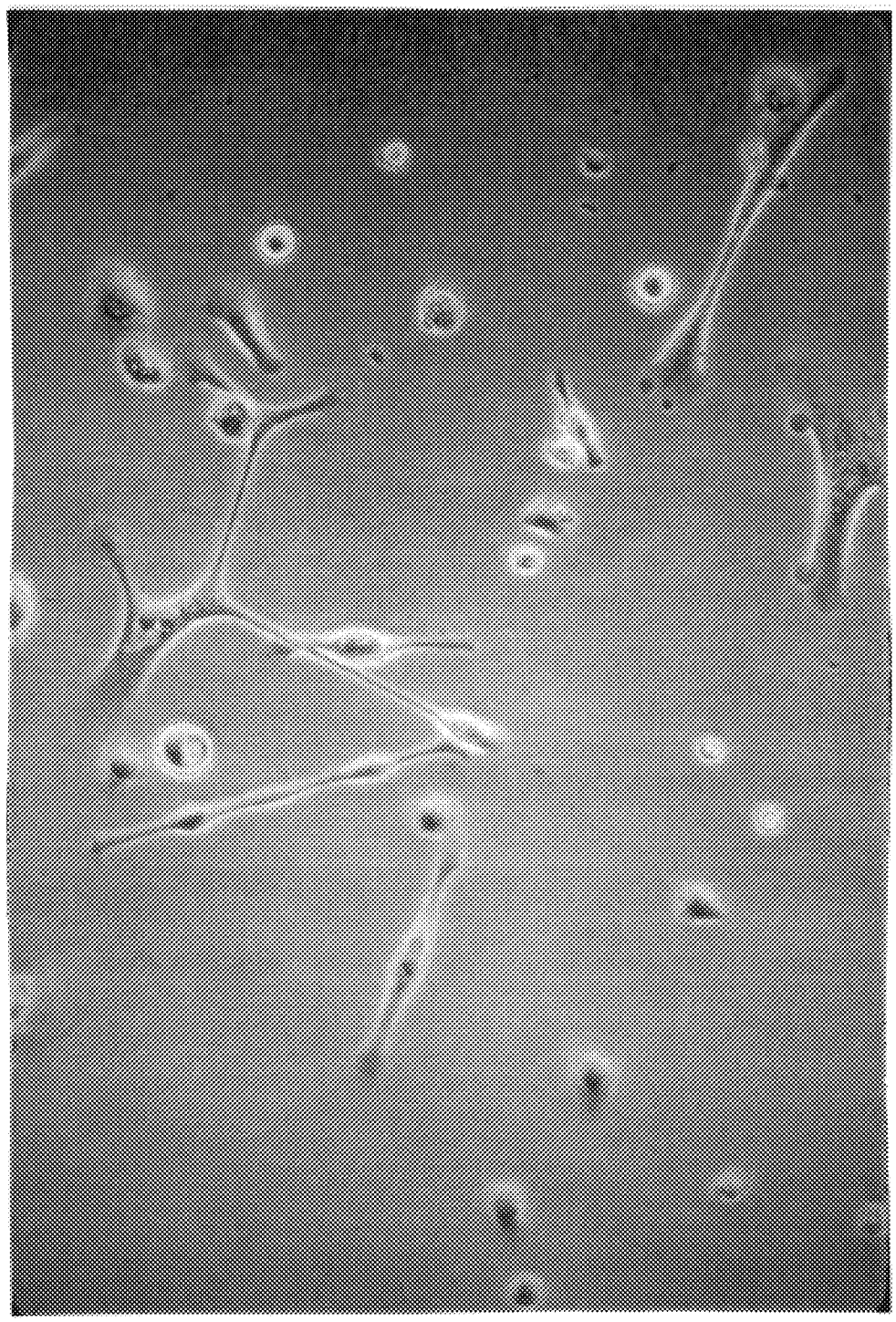
Figure 1E:
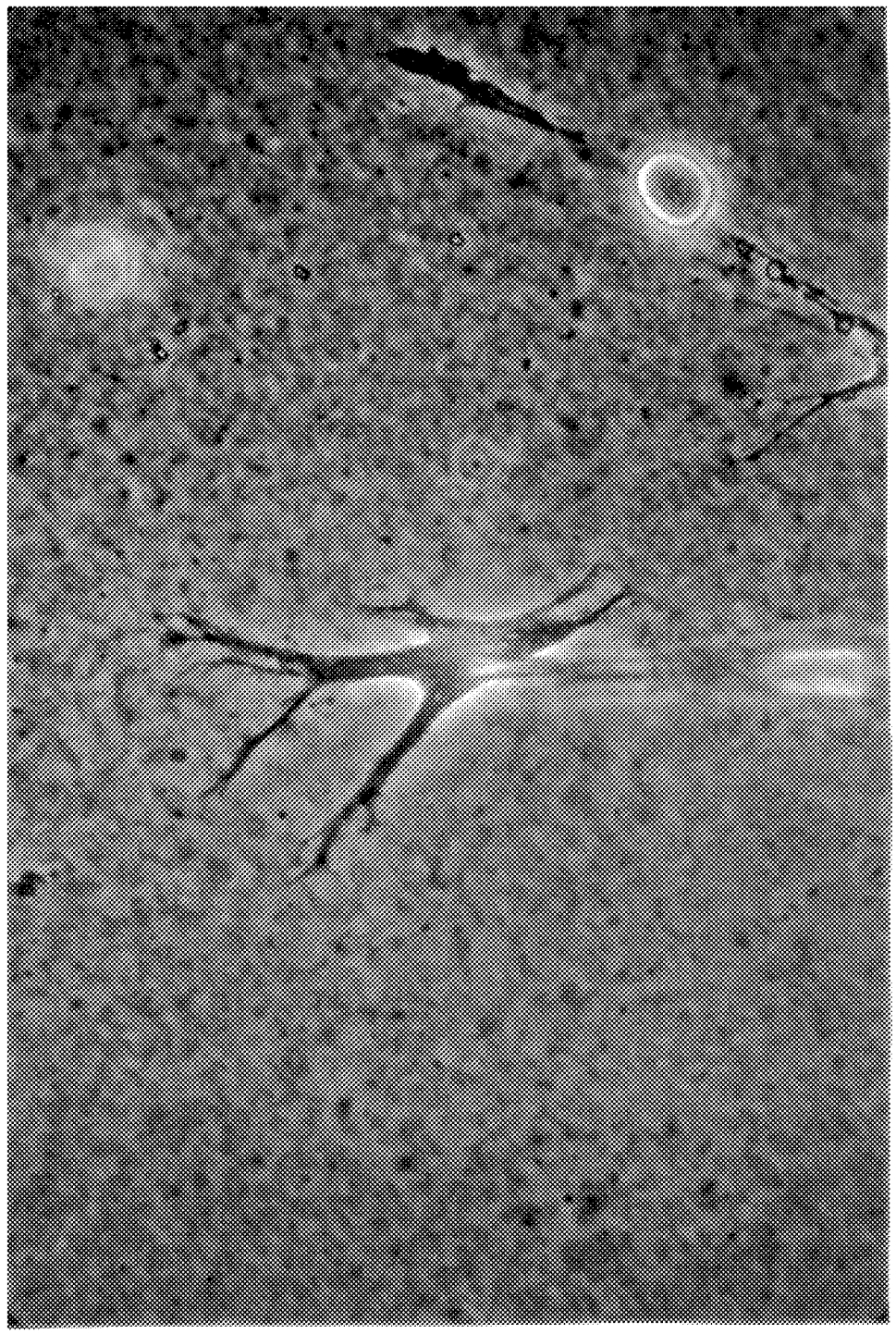

The present invention relates to cultures of human olfactory neurons and uses thereof. In one embodiment of the present invention, cultures of human olfactory neurons are established from human tissue samples containing neurons, such as nasal epithelium. Suitable tissue samples are obtained from the cadavers of healthy individuals that is to say individuals without any central nervous system diseases. Cultured neurons thus obtained display normal neuronal pathology and express several neuron specific proteins (eg. neuron specific enolase, neurofilament (68 KD form) and tau protein).

In another embodiment of the present invention, cultures of human olfactory neurons are established from a tissue sample obtained from the cadavers of individuals with Alzheimer's disease. It is anticipated that these cultures of neurons will display the pathology associated with Alzheimer's disease [Talamo et al., Nature 337:736–739, (1989)]. As one skilled in the art will appreciate, cultures of neurons can be established using the method of the present invention from an individual afflicted with any generalized central nervous system disease which includes neurological and psychiatric illnesses such as Parkinson's disease, Tay-Sachs disease, schizophrenia, manic-depression, depression or mental retardation. A generalized central nervous system disease affects many types of neurons in the central nervous system including olfactory neurons. These cultured neurons may display the pathology of the disease affecting the individual from which the culture was grown.

In a preferred embodiment, the neuron cultures are established utilizing a basement membrane. The basement membrane consists mainly of laminin and collagen. Therefore, the present invention contemplates cultured human neurons which are initially grown and/or maintained on a membrane of laminin, collagen, related peptides thereof or a combination of the foregoing. When maintained under conditions allowing growth in three dimensions in the membrane the neurons appear more differentiated.

The neurons of the present invention are grown in Coon's 4506 medium. In addition to neurons, Coon's 4506 medium has been shown to support the growth of other human and rat cells. For example, using standard culture techniques and Coon's 4506 medium, human Pancreatic Islet cells, human cervical carcinoma cells, a colon cancer cell strain and rat cells have been grown. The present invention also relates to cultures of transformed human olfactory neurons. One skilled in the art can easily transform and thereby immortalize cultured human olfactory neurons of the present invention without undue experimentation. Cultured neurons of the present invention can be transformed using, for example, the basic protocol described by Fredericksen et al. [Neuron 1:439–448, (1988)]. Neurons can be transformed using a retroviral vector, such as pzipNeoSVC(X), which contains a temperature sensitive form of the SV40 large T antigen ts A58; the large T antigen is an oncogene. The transformed neurons will proliferate indefinitely in a relatively undifferentiated state at the permissive temperature of 33° C. but will be able to differentiate into neurons at the nonpermissive temperature of 39° C.

In another embodiment of the present invention, cultured neurons from an individual with a central nervous system disease are used for screening drugs for their ability to reverse or eliminate the disease pathology. The cultured neurons are contacted with various drugs under conditions such that reversal or elimination of the disease pathology can be effected by the drug if it has the ability to do so.

For example, levels of dopamine receptors and/or receptor function in cells from a schizophrenic individual can be compared to that of normal individuals. If differences are found, then these differences can be used in assays to study the disease and to screen for drugs that correct the alteration. The presence of paired helical filaments or other Alzheimer's related antigens such as A68 can be used to assay for Alzheimer's disease pathology [Wolozin et al., Science 232:648–650, (1986)]. In manic-depression alterations in G protein function are hypothesized. Neurons of the present invention cultured from an individual with manic-depression can be used to screen for drugs correcting the G protein misfunction. Cultured neurons can also manifest the disorder present in gangliosidoses like Tay-Sachs disease, inherited forms of mental retardation or other inherited neurologic diseases [Adams et al., Principles of Neurology. (McGraw-Hill, New York. 1985). pp.718–759]. Neurons of the present invention can be used to screen for drugs decreasing the build up of gangliosides.

The ability of drugs to reverse or eliminate Alzheimer's disease can be determined by their ability to reduce or eliminate the production of Alzheimer specific proteins, such as amyloid precursor proteins (APPs) and A68 protein. For testing potential therapeutically active compounds, cultured neurons from an individual with Alzheimer's disease are contacted with various drugs under conditions such that production of the specific proteins can be effected. Reduction or elimination of APPs or A68 is detected by preincubating the cultures in a calcium salt, such as $CaCl_2$, and then contacting the cultured neurons with a calcium ionophore, such as CA23187 or ionomycin, at a concentration sufficient to activate calcium dependent proteins. Calcium is a second messanger in the cells. The stimulation of other second messangers may also elicit Alzheimer's specific changes.

The presence or absence of APPs or A68 is detected by methods known in the art, for example, immunoblot techniques using an anti-A4 antibody or Alz-50 antibody. In addition, probes to the Alzheimer specific proteins can be developed using cloning, PCR or immunologic methods to facilitate detection.

Neurons of the present invention which naturally or through a modification secrete dopamine can be used for injection into the sybstantia nigra of individual with Parkinson's disease.

In another embodiment of the present invention, cultured neurons are used to screen for drugs that inhibit viral activity in neurons. Neurons of the present invention are contacted with a virus which naturally infects human neurons, such as the herpes virus or cytomegalovirus (CMV), and with various drugs under conditions such that inhibition of viral function can be effected. Drugs which inhibit virus attachment, penetration, replication or toxicity can be screened for and could be use in treatment or prevention of such infections.

Rat olfactory neurons can be stimulated to release the calcitonin gene related peptide (CGRP) by altering potassium levels when incubated with a neurotoxin. Release of CGRP may be a sensitive indicator of neurotoxicity. Human olfactory neurons of the present invention containing CGRP or any other neurotransmitter can be used to assess the neurotoxicity of an agent by detecting alterations of basal and potassium evoked neurotransmitter release into the medium in the presence and absence of the agent. Neurotoxicity may correlate with a decline in neurotransmitter release over time as neuronal function deteriorates.

In another embodiment of the present invention, the cultured neurons are used for testing the neurotoxicity of an agent in humans. As one skilled in the art will appreciate, determining the effect of the agent on any of a number of neuronal characteristics will reflect that neurotoxicity of the agent. For example, the concentration of the agent producing death in 50% of the neurons (LD50) can be determined using methods known in the art. The effect of the agent on neuronal growth characteristics such as population doubling time and length of processes also reflect the toxicity of the agent to humans.

In a further embodiment of the present invention, cultured neurons are used for the diagnosis of central nervous system diseases. Neurons are obtained from an individual suspected of having a central nervous system disease and cultured according to the present invention. The presence or absence of diseased state proteins is then detected. The individual would be diagnosed with the disease if the proteins are detected. For example, Alzheimer's can be diagnosed by the detection of APPS. Neurons from an individual which are cultured in accordance with the present invention, are incubated in a calcium salt and then contacted with a calcium ionophore. The presence or absence of APPs is detected using standard methods known in the art.

For purposes of illustrating a preferred embodiment of the present invention, in the following non-limiting example, cultures of olfactory neurons from individual without central nervous system diseases and from individuals with Alzheimer's disease were established. It is, however, to be understood that the discussion generally applies to established cultures of neurons from individuals with any central nervous system disease.

EXAMPLE

Procurement of Olfactory Epithelium

Olfactory epithelium was procured from cadavers of healthy individuals and Alzheimer's individuals using a cup shaped curette 6 cm in length and with a curette size of 5 or 7.5 mm (depending on the size of the nasal passage).

One of the two approaches (Anterior or Posterior) was taken to obtain epithelium containing olfactory neurons. In the "Anterior" approach, the curette was advanced into the nasal vestibule. The curette was then placed adjacent to the first nasal turbinate (concha) encountered. The first turbinate was usually encountered after the curette was advanced about 3 or 4 cm into the nasal vestibule.

The turbinate was scraped 3 or 4 times with the curette. Olfactory epithelium, yellower than the surrounding tissue was obtained. Since the olfactory tissue lies over the bone, the presence of some bone associated with the scrapings is a good sign.

The tissue was placed in modified L-15 transport medium containing polyvinylpyrrolidone-360 200 mg/l, glutathione 0.79 mg/l, 2-mercaptoethanol 50 mg/l, fetal bovine serum 1%, penicillin 200 U/ml, streptomycin sulfate 200 mcg/ml (all above agents were from Sigma or GIBCO) and fungizone 2.5 ug/ml (Squibb). The tissue was transported on ice. However, the sample was not frozen since freezing kills the tissue.

As an alternative to the modified L-15 transport medium described above, the L-15 transport medium may be modified to contain some or all of the agents described by Kischer et al. [Cytotechnology 2:181–185, (1989)].

Procurement of olfactory epithelium using the "Posterior" approach was somewhat more difficult than with the "Anterior" approach.

The olfactory epithelium lies underneath the cribriform plate and sends axons up through the plate into the olfactory bulb. Therefore, the portion of the cribiform plate immediately underneath the olfactory bulb was removed and the tissue underneath collected. It was not necessary to separate the tissue from the attached bone; however, the dura had to be removed.

The collected tissue was transported as described above in the "Anterior" procurement approach.

Olfactory Neuron Culturing

The olfactory neurons were grown using the basic method described by Coon et al. [PNAS USA 86:1703–1707, (1989); see also Ambesi-Impiombato et al. PNAS USA 77:3455–3459, (1980)]. The collected tissue was cut into 1 mmx 1 mm pieces and put under a reconstituted basement membrane preparation available as "matrigel" (Collaborative Research Inc.) and kept in Coon's 4506 medium.

Coon's 4506 medium uses modified Ham's F-12 medium as a base. Coon's 4506 is made by first preparing Coon's modified Ham's F-12 to include the amino acids, salts and minerals described below in the Table 1. The modified Ham's F-12 is then further modified by including the items listed below in Table 2 to generate Coon's 4506 medium.

TABLE 1

Coon's Modified Ham's F-12 - neuroblast formulation**

| Component | grams per liter |
|---|---|
| L-Alanine | 0.018 |
| L-Arginine HCl | 0.420 |
| L-Asparagiane Anhyd | 0.030 |
| L-Aspartic Acid | 0.026 |
| L-Cysteine HCl—$H_2O$ | 0.070 |
| L-Glutamic Acid | 0.030 |
| L-Glutamine | 0.290 |
| Glycine | 0.160 |
| L-Histidine HCl—$H_2O$ | 0.042 |
| L-Isoleucine | 0.008 |
| L-Leucine | 0.026 |
| L-Lysine HCl | 0.073 |
| L-Methionine | 0.009 |
| L-Phenylalanine | 0.010 |
| L-Proline | 0.070 |
| L-Serine | 0.021 |
| L-Threonine | 0.024 |
| L-Tryptophan | 0.004 |
| L-Tyronsine 2Na | 0.016 |
| L-Valine | 0.023 |
| D-Glucose | 2.00 |
| Biotin | 0.00007 |
| D-Ca Pantothenate | 0.0005 |
| Choline Chloride | 0.014 |
| Folic Acid | 0.001 |
| Myo-inositol | 0.036 |
| Niacinamide | 0.00004 |
| Pyridoxine HCl | 0.00006 |
| Riboflavin | 0.00004 |
| Thiamine HCl | 0.00029 |
| Vitamin B-12 | 0.0014 |
| Putrescine 2HCl | 0.0003 |
| Na Pyruvate | 0.220 |
| Na Hypoxanthine | 0.0047 |
| Thymidine | 0.0007 |
| L-Ascorbic Acid | 0.045 |
| Linoleic Acid | 0.00009 |
| Lipoic Acid | 0.0002 |
| Phenol Red | 0.0012 |
| Sodium Chloride | 7.530 |
| Potassium Chloride | 0.230** |
| Sodium Phosphate Dibasic Anhyd | 0.135 |
| or as - $7H_2O$ | 0.250 |
| Potassium Phosphate Monobasic | 0.068 |
| Magnesium Chloride - $6H_2O$ | 0.081** |
| Magnesium Chloride - $7H_2O$ | 0.025** |
| Calcium Chloride | 0.0** |
| Cupric Sulfate - $6H_2O$ | 0.000002 |
| Ferrous Sulfate - $7H_2O$ | 0.0008 |
| Zinc Sulfate - $7H_2O$ | 0.000144 |

TABLE 2

Coon's 4506 Medium

MODIFIED F12 (mF12. neuroblast formulation)
[Ham's F12 with the following changes:]

2 times the concentration of AMINO ACIDS,
PYRUVATE                                    45 µg/ml
ASCORBATE
HANK'S SALTS in place of those specified by Ham
Hank's formulation further modified so as to TABLE 2-continued Coon's 4506 Medium

| contain | |
|---|---|
| Mg++ – 0.48 mM | |
| NO ADDED Ca++ (Final ≦ 0.1 mM from extracts) | |
| KCl reduced | 0.230 mg/ml |
| FOLIC ACID | 0.001 mg/ml |
| HYPOXANTHINE | 0.0047 mg/ml |
| THYMIDINE | 0.0007 mg/ml |
| GLUCOSE | 2 mg/ml |
| GALACTOSE | 0.5 mg/ml |
| NO LINOLEIC ACID | |
| ADDITIVES to make 4506 from mF12 base: | |
| FETAL BOVINE SERUM (GIBCO) | 60% |
| TRANSFERRIN (HUMAN) | 5 μ/ml |
| INSULIN (Na+) | 1 μ/ml |
| HYDROCORTISONE | 3.5 ng/ml |
| SELENOUS ACID | 2.5 ng/ml |
| THYROXINE $T_3$ | 40 pg/ml |
| GENTAMYCIN $SO_4$ (GIBCO) | 50 μg/ml |
| EXTRACTS (final concentrations): | |
| BOVINE HYPOTHALAMUS | 150 μg protein/ml |
| BOVINE pituitaryMUS | 50 μg protein/ml |
| CULTURES made in droplets or on plates coated with: | |
| "BASEMENT MEMBRANE" (e.g. "Martrigel" Collaborative Research, Inc.) | ~150 μg protein/ml |

The above concentrations of Mg++, Ca++, KCl, transferrin, insulin, hydrocortisone, selenous acid, and gentamycin $SO_4$ can, advantageously, be varied by ±10%; the above concentrations of ascorbate, folic acid, hypoxanthine, thymidine, glucose, galactose, fetal bovine serum, $T_3$, bovine extracts and basement membrane can, advantageously, be varied by ±50%. Variations in the preferred ranges indicated above, as one skilled in the art will appreciate, may be acceptable and/or advantageous depending, for example, on the cell type to be grown. The optimal concentrations can readily be determined.

After several weeks of culture, neurons began to grow. A variable number of tissue pieces, between 10–100% grew out neurons. Neuronal cultures were selected based on the morphology of the cells. Other types of cells that grew out were epithelial, glandular and a spindly type. (See FIG. 1). The basement membrane functioned to inhibit growth of other cell types and promote neuronal growth.

The neurons were collected as in Coon et al. [PNAS USA 86:1703–1707, (1989)] and grown in cell culture dishes coated with basement membrane. Dishes were coated with basement membrane by spreading cold basement membrane on the dish and then leaving the dish at 37° C. for at least 10–20 minutes. The Coon's 4506 medium was changed twice a week. Cells were not allowed to remain confluent for more than 2 days. The neurons were harvested from the dishes by treating the neuron cultures with a protease solution, Dispase (Boehringer-Mannheim, Indianapolis) for 1 hr at 37° C. The medium containing the detached cells was spun down at 1000 rpm for 10 min, the supernatant removed and then the cells were resuspended in appropriate medium. Cells were always placed onto plates coated with basement membrane solution.

For storage, cells were in Coon's 4506 medium containing 10% dimethylsulfoxide. Cells were frozen down under liquid nitrogen.

Clonal colonies of neurons were also obtained by diluting harvested neurons in Coon's 4506, growing them on basement membrane coated dishes, isolating individual colonies using cloning cylinders (BellCo) and then harvesting individual colonies as described above.

Coon's 4506 medium was required for initial growth of the neurons. Once established, the culture may be able to be maintained using other mediums such as Keratinocyte Growth Medium (Clonetics, San Diego) instead of the Coon's 4506.

Identification of Neuronal Cells

Figure 2:
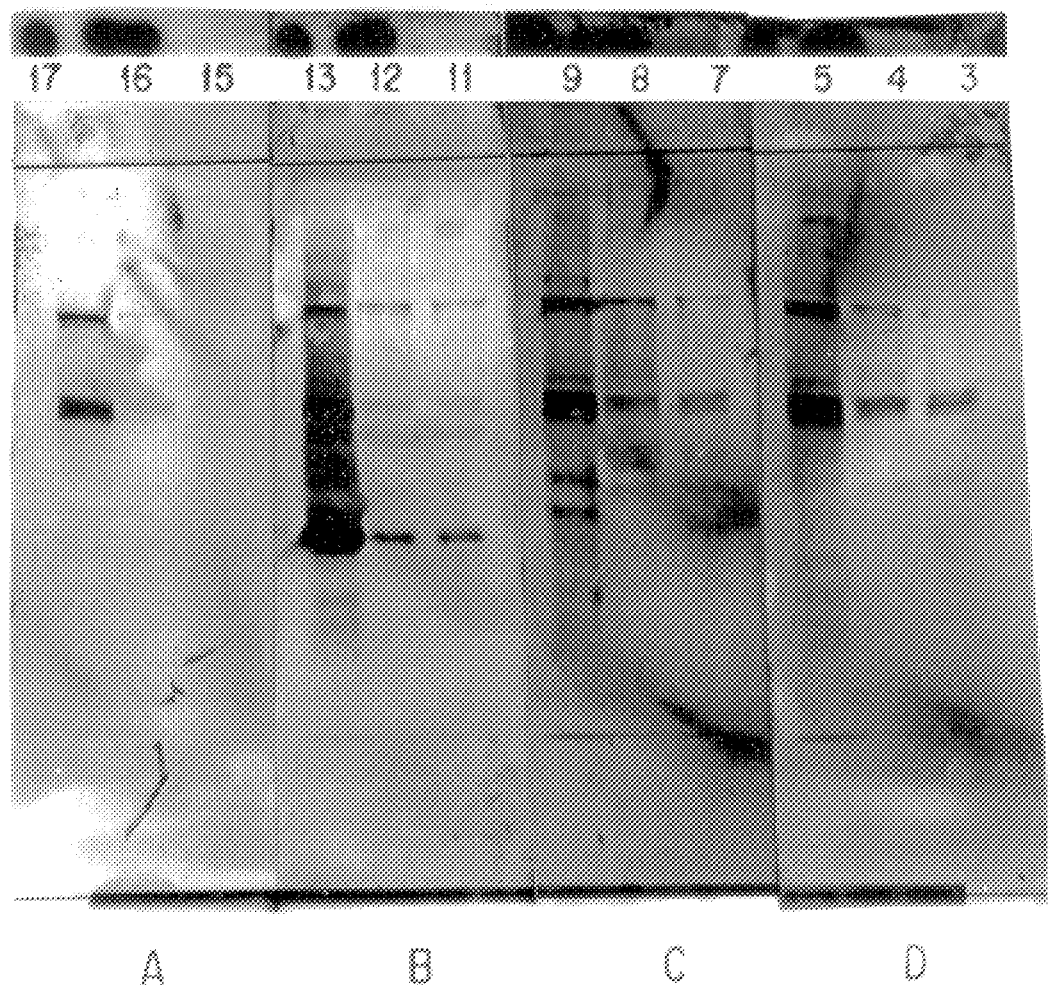
FIGS. 2A–2D show Western Blots of neuron specific proteins.

Neuronal cells were identified using immunocytochemistry and western blot methodologies well known in the art. The cells were shown to express several neuron-specific proteins: Neuron Specific Enolase, Neurofilament (68 KD form) and Tau Protein (see FIG. 2).

From a tissue sample containing only neurons, a pure neuron population was grown out without the aid of the basement membrane. The Coon's 4506 had an increased amount of fetal bovine serum (20%) and culture growth was slower.

Human olfactory neurons strains 1402 and 90-1 were deposited on Mar. 6, 1990 under the Budapest Treaty at the American Type Culture Collection, 12301 Parklawn Drive, Rockville, Md. 20852.

Detection of Altered Amyloid Precursor Protein (APP) Metabolism

To detect APP metabolism and identify Alzheimer's diseased olfactory neurons, olfactory neurons from patients with Alzheimer's disease were cultured as described above. The cultured neurons were preincubated for 24 hours in a final concentration of 3 mM $CaCl_2$. While $CaCl_2$ was used, it is believed other calcium salts may also be utilized at concentrations as low as 1 mM.

After preincubation, the calcium ionophore CA23187 was added to the neuron culture at a final concentration of 100 nM. The ionophore was added to elevate intracellular calcium in order to activate calcium dependent proteins. It is believed concentrations of ionophore as low as 10 nM may be effective. The culture was then incubated for 24 hours. Some effect was seen after 1–4 hours, however, a greater effect was seen after 24 hours of incubation.

The incubated neurons were homogenized and a standard immunoblot assay was preformed using anti-A-4 antibody (Boehringer Mannheim, Indianapolis, IN). (Anti-A4 recognizes the all region common to all APPs.) 60 μg per lane were electrophoresized on a 8% or 10% polyacrylamide gel and transferred to nitrocellulose. Nonspecific binding was blocked with bovine serum albumin prior to treatment with anti-A4 antibody. A phosphatase coupled avidin-biotin conjugate kit (Vector Labs, Burlingame, Calif.) to visualize APP species. The Alzheimer's disease specific reactivity, that is anti-APP reactivity, was seen at 100±10 KD.

The entire contents of all references cited hereinabove are hereby incorporated by reference.

While the foregoing invention has been described in some detail for purposes of clarity and understanding, it will be clear to one skilled in the art from a reading of this disclosure that various changes in form and detail can be made without departing from the true scope of the invention.

What is claimed is:

1. A method of diagnosing Alzheimer's disease comprising the steps of:
   i) isolating human tissue containing olfactory neurons;
   ii) growing said tissue in a suitable medium under a first membrane comprising collagen and laminin, establishing a human olfactory neuron culture;
   iii) separating said first membrane from neurons;
   iv) replating said neurons on a surface coated with a second membrane comprising collagen and laminin;
   v) culturing said neurons of step (iv) under conditions; allowing replication;
   vi) contacting said cultured neurons with a calcium salt;
   vii) contacting said neurons of step (vi) with an ionophore;
   viii) detecting AD-specific changes in amyloid precursor protein or A68 as compared to normal; and
   ix) diagnosing tissue as AD afflicted, if any AD-specific changes of said proteins of step (viii) are detected.

2. The method according to claim 1 wherein said ionophore is CA23187 or ionomycin.

3. The method according to claim 1 wherein said medium is Coon's 4506 medium.

* * * * *